(12) United States Patent
Schaer

(10) Patent No.: US 6,251,107 B1
(45) Date of Patent: *Jun. 26, 2001

(54) EP CATHETER

(75) Inventor: Alan K. Schaer, San Jose, CA (US)

(73) Assignee: Cardima, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/104,752

(22) Filed: Jun. 25, 1998

(51) Int. Cl.$^7$ .................................................. A61B 18/18
(52) U.S. Cl. ........................ 606/41; 600/374; 600/549; 607/99; 607/113; 607/122
(58) Field of Search .......................... 606/41; 600/374, 600/381, 383, 549; 607/99, 113, 122

(56) References Cited

U.S. PATENT DOCUMENTS

| | | | |
|---|---|---|---|
| 4,966,597 | 10/1990 | Cosman | 606/50 |
| 5,373,850 | * 12/1994 | Kohno et al. | 128/692 |
| 5,500,012 | 3/1996 | Brucker et al. | 607/122 |
| 5,531,781 | * 7/1996 | Alferness et al. | 607/122 |
| 5,549,109 | * 8/1996 | Samson et al. | 128/642 |
| 5,582,609 | 12/1996 | Swanson et al. | 606/39 |
| 5,682,899 | * 11/1997 | Nashef et al. | 600/505 |
| 5,706,809 | * 1/1998 | Littmann et al. | 600/381 |
| 5,769,847 | * 6/1998 | Panescu et al. | 606/42 |
| 5,885,278 | * 3/1999 | Fleischman | 606/41 |
| 6,129,724 | * 10/2000 | Fleischman et al. | 606/41 |

* cited by examiner

Primary Examiner—Lee Cohen
(74) Attorney, Agent, or Firm—Heller Ehrman White & McAuliffe LLP

(57) ABSTRACT

A low profile intravascular electrophysiology (EP) device for the formation of linear lesions which has particular utility in the treatment of atrial fibrillation and flutter. The EP device of the invention has an elongated shaft with a proximal section, a distal section, and a plurality of at least partially exposed electrodes disposed on an outer surface of the distal section. The electrodes are spaced along a length of the distal section with at least one temperature sensor located between adjacent electrodes. High frequency, e.g. RF, electrical energy delivered to the electrodes on the distal shaft section of the EP device will form a linear lesion which terminates the fibrillation or flutter.

35 Claims, 3 Drawing Sheets

EP CATHETER

BACKGROUND OF THE INVENTION

This invention generally relates to the detection and elimination of cardiac arrhythmia and particularly atrial fibrillation and atrial flutter.

Atrial fibrillation is the disorganized depolarization of a patient's atrium with little or no effective atrial contraction. This condition may be chronic or intermittent, and it presently affects approximately 2 million people in the United States alone. Prior methods for treating a patient's arrhythmia include the use of antiarrhythmic drugs such as sodium and calcium channel blockers-or drugs which reduce the Beta-adrenergic activity. Other methods include surgically sectioning the origin of the signals causing the arrhythmia or the conducting pathway for such signals. However, the surgical technique is quite traumatic and is unacceptable to a large number of patients. A more frequently used technique to terminate the arrhythmia involves destroying the heart tissue which causes the arrhythmia by heat, e.g., applying a laser beam or high frequency electrical energy, such as RF or microwave, to a desired arrhythmogenic site on the patient's endocardium. In the latter method, intravascular electrophysiological (EP) devices can be used to form contiguous lesions within a patient's atrial chamber to provide results similar to the surgical segregation techniques in terminating atrial fibrillation but with significantly reduced trauma.

Typically, the EP device is advanced within a patient's vasculature and into a heart chamber, and a lesion is formed at the endocardium when RF electrical energy is emitted from electrodes of the device. RF ablation techniques produce lesions of a significantly smaller area. Consequently, several lesions are typically formed to completely ablate an area than the average arrhythmogenic site. A major problem of RF ablation techniques is forming a lesion of the requisite size, which completely ablates the area of interest but does not unnecessarily destroy surrounding healthy tissue.

What has been needed is an ablation device which allows for improved monitoring of the creation of a lesion, to generate linear lesions of a requisite length. The present invention satisfies these and other needs.

SUMMARY OF THE INVENTION

This invention is directed to a low profile electrophysiology (EP) device suitable for forming linear ablations within a chamber of a patient's heart. The EP device of the invention has electrodes and temperature sensors along an outer surface of the device. The configuration results in a low profile and improved control over lesion size due to improved monitoring of lesion formation. The lesions from such linear ablations are particularly suitable for eliminating or minimizing atrial fibrillation and flutter by isolating sections of the patient's atrial wall.

The EP device of the invention generally comprises an elongated shaft with a proximal section, a distal section, and a plurality of at least partially exposed electrodes disposed on an outer surface of the distal section. The electrodes are spaced along a length of the distal section with at least one temperature sensor located between adjacent electrodes.

The electrodes on the distal shaft section form a lesion from within a patient's heart chamber when electrical energy, preferably RF energy, is emitted therefrom. The electrodes may be combination sensing and ablation electrodes which are capable of ablation and detection of electrical activity from within a lumen of the patient's body. In a preferred embodiment, the electrodes on the device shaft are independent, for monopolar mode use with an electrode in contact with the exterior of the patient's body. Alternatively, the electrodes may be bipolar, for use as a pair of electrodes on the shaft. A presently preferred electrode is in the form of a helical coil for improved device flexibility, although other designs are suitable including cylindrical bands, arcuate bands or ribbons or the like. For high resolution sensing, the electrodes may be spaced in a first compact array of electrodes mounted on the distal shaft section and a second expanded array of sensing electrodes mounted on the distal shaft section with an interelectrode spacing greater than that of the first compact array, such as described in copending application Ser. No. 08/443,657, entitled High Resolution Intravascular Signal Detection, filed on May 18, 1995, which is incorporated herein in its entirety.

A presently preferred temperature sensor is a thermocouple, although other suitable temperature sensors may be used, such as thermisters or other temperature sensing means. The presently preferred thermocouple is a T-type formed of copper and constantan wire. A conducting member may be provided on an outer surface of the temperature sensor. The conducting member is formed from a conducting material, such as gold, which rapidly equilibrates the temperature around the catheter circumference to the temperature at the patient's heart wall.

The location of the temperature sensors on an outer surface of the device between the electrodes allows for a low profile device. The low profile facilitates maneuvering and positioning the operative distal end of the device within the patient. The maximum outer diameter of the distal shaft section of the device is about 1.0 mm (3.0 French) to about 1.3 mm (4 French). In contrast to the EP device of the invention, EP devices having temperature sensors radially spaced in the shaft, at a location intermediate the electrodes and the central axis of the device, require a larger diameter shaft than the EP device of the invention.

Moreover, the EP device of the invention provides more effective lesion formation through improved monitoring of the temperature during lesion formation. To effectively ablate an arrhythmogenic site, the individual lesions formed by adjacent electrodes must come together, in order to form one continuous lesion that completely ablates an area of interest. However, if lesion formation is prematurely stopped, the lesions will not be continuous and thus may not terminate the arrhythmia. EP devices having temperature sensors located distal or proximal to the section of the shaft on which the electrodes are located, or radially spaced from the electrodes within the device shaft, cannot accurately measure the temperature of the heart wall between adjacent electrodes, and consequently do not effectively monitor the ablation to ensure a continuous lesion. In contrast, with the EP device of the invention, the temperature sensors monitor the temperature of the heart wall at the edge of the adjacent lesions which meet or overlap to form one continuous lesion. By thus monitoring the temperature, the physician is able to ensure that adequate heating is produced, while avoiding over heating which could cause coagulation of blood and charring of tissue. Thus, the physician applies ablation energy to adjacent electrodes so that the heart wall between the electrodes reaches a given temperature for a given time. In this way, the physician can monitor lesion formation and determine when one continuous lesion of the desired size has been formed.

The wall of the distal section is formed at least in part of individually insulated electrical conductors which are electrically connected to individual electrodes on the distal section. Preferably the electrical conductors are braided. Individual conductor wires in the distal section wall are also connected to the temperature sensors, or, in the case of thermocouple temperature sensors, have a distal end which forms the temperature sensor. A plurality of polymer strands formed of nylon, DACRON® (Dupont) and the like may also be braided either with the electrical conductors as they are braided or braided separately on the exterior of the tubular member formed by the braided conductors. The proximal ends of the electrical corductors are electrically connected to individual pins of a multi-pin connector on the proximal end of the shaft which facilitate transmission of high frequency electrical energy from a source thereof to individual electrodes (if an extracorporeal electrode is used) or pairs of electrodes. The multi-pin connector on the proximal end of the shaft is also configured to be connected to a receiving member in electrical communication with a display unit which can display representations of the electrical activity sensed.

In a presently preferred embodiment of the invention, the EP device of the invention is in the form of a guidewire which has an elongated core member disposed within the device shaft. The distal section of the guidewire may have a flexible guide tip which is distal to the length on which the electrodes are mounted. The distal guide tip may have a helical coil which is disposed about the distal extremity of the core member or a separate shaping member, e.g., a ribbon, which extends from the distal extremity of the core member. The distal end of the core member or the separate shaping member may be manually shaped by the physician to facilitate steering the elongated sensing device within the patient's vasculature by torquing the proximal end which extends out of the patient during the procedure. A smooth rounded tip or plug is provided at the distal end of the coil to avoid damage to a blood vessel when being advanced through the patient's vascular system. Conventional guidewire construction may be employed. An electrode-may be provided on the distal end of the EP device and the core member is used to transmit electrical current to the electrode on the distal end.

The core member is preferably provided with one or more jackets, which may be electrically insulating. This design allows for a low profile and flexibility, yet it is sufficiently strong to ensure effective contact between a length of the electrode section and the region of the patient's endocardium where the ablation is to occur and an effective formation of an arrhythmia terminating lesion. The individually insulated electrical conductors may be at least in part within an outer jacket of the core member.

The elongated device of the invention may also be in the form of a catheter which has an elongated inner lumen extending from the proximal end to a discharge or guidewire port in the distal end of the device. The distal end of the catheter may be provided with a soft tip to minimize traumatic engagement with a blood vessel wall when being advanced therein. In one presently preferred embodiment, the inner lumen of the catheter form of the device is configured to allow the passage there through of a conventional guidewire or a guidewire version of the device of the invention which allows signal detection at different locations within the same blood vessel or branch thereof such as described in copending application Ser. No. 08/188,298, entitled Method and System for Using Multiple Intravascular Sensing Devices to Detect Electrical Activity, filed on Jan. 27, 1994, which is incorporated herein in its entirety.

The EP device of the invention may be used alone or with a variety of shaped or shapeable guide members. In one presently preferred embodiment, the EP device is used with a deflectable guiding catheter having a lumen which slidably receives the EP device of the invention and a distal section that can be deflected in either of two directions away from the guiding catheter longitudinal axis, such as described in copending application Ser. No. 09/001,249, filed on Dec. 30, 1997, entitled Deflectable Guiding Catheter, Jay J. Qin, Duane Dickens, Laurent Schaller, inventors, which is incorporated herein in its entirety.

The EP device of the invention may also be used with a guiding member having an elongated open distal section such as described in copending applications Ser. No. 08/629, 057, filed on Apr. 8, 1996, and Ser. No. 08/659,769, filed on Jun. 6, 1996, entitled Linear Ablation Assembly, which are incorporated herein in their entirety. Longitudinal movement of the EP device disposed within the lumen of the delivery sheath causes the distal section of the EP device to arcuately extend out and away from the open distal section of the delivery sheath, and effectively contact the surface of the patient's heart chamber for effective linear ablation of heart tissue.

The EP catheter of the invention has a low profile for improved maneuverability due to the location of temperature sensors along an outer surface of the device shaft between electrodes. The location of the temperature sensors also provides for effective monitoring of the lesion formation, which allows for improved control over the lesion size, resulting in complete ablation of an area of interest without the undesirable destruction of surrounding tissue. These and other advantages of the invention will become more apparent from the following detailed description and the accompanying exemplary drawings.

DETAILED DESCRIPTION OF THE INVENTION

Figure 1:
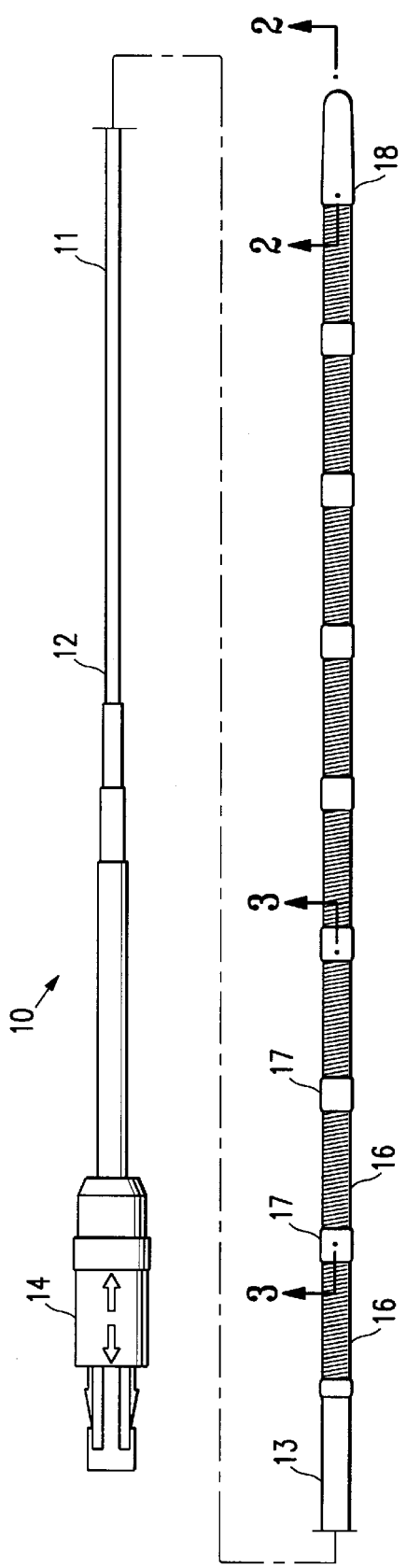
FIG. 1 is an elevational view of an EP device embodying features of the invention.

As shown in FIG. 1 the EP device 10 of the invention generally comprises an elongated shaft 11 having proximal and distal shaft sections 12 and 13, an electrical connector 14 on the proximal end of the device, a plurality of electrodes 16 on the distal shaft section 13, a plurality of temperature sensors 17 on the distal shaft section with at least one temperature sensor between the electrodes 16, and a soft flexible tip 18 on the distal end of the device. In the embodiment illustrated in FIG. 1, the electrodes and temperature sensors are in an alternating arrangement with one temperature sensor between two adjacent electrodes.

Figure 2:
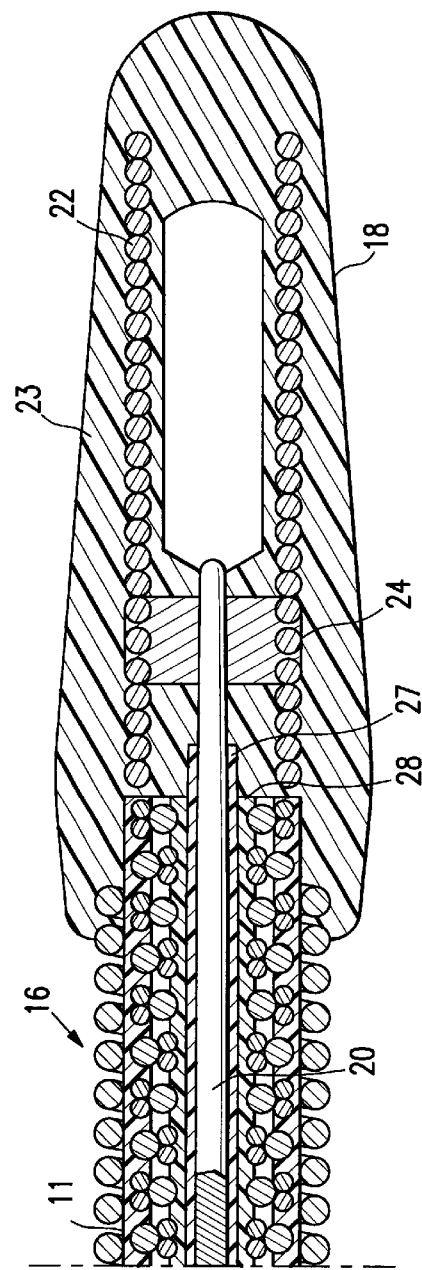
FIG. 2 is an enlarged longitudinal cross-sectional view of the EP device shown in FIG. 1 taken along the lines 2—2.
Figure 3:
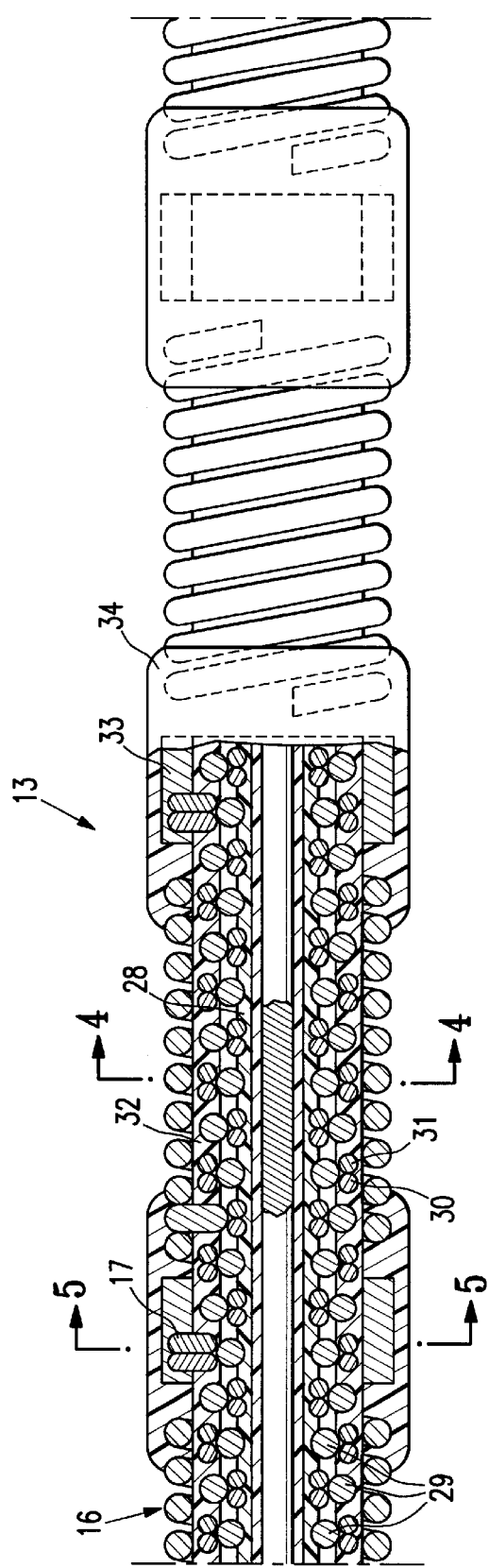
FIG. 3 is an enlarged longitudinal view, partially in section, of the EP device shown in FIG. 1 taken along the lines 3—3.

In the embodiment illustrated in FIG. 1, the EP device 10 is in the form of a guidewire. As best illustrated in FIG. 2, showing an enlarged longitudinal cross-section of the EP device shown in FIG. 1, a core member 20 extends within the shaft 11 to the distal end of the device. The soft flexible tip 18 has a closed distal end, and includes a flexible coil 22 extending beyond the distal end of the shaft 11 enclosed within a soft coating 23 preferably formed of a polymeric material. In the embodiment illustrated in FIG. 2, tip 18 has an open center region for increased flexibility. A presently preferred polymeric material for the tip 18 is a fluoropolymer such as THV available from 3M. The core member 20 is secured to the distal end of the coil 22 at 24 by suitable material such as gold-tin solder (80% Au—20% Sn). The core member 20, and preferably a distal section thereof, may be tapered as shown, or optionally flattened.

A catheter form of the device (not shown) is similar to the guidewire form shown in FIG. 1, except that core member 20 is omitted, and a lumen is provided extending within the shaft 11 which is configured to receive a guidewire or other device therein The core member 20 is preferably a stainless steel wire with a maximum diameter of about 0.01 inch (0.25 mm) to about 0.018 inch (0.46 mm). The core member 20 is provided with one or more jackets having a total thickness of preferably less than about 0.001 inch (0.025 mm). In a presently preferred embodiment, the core member jacket comprises an insulating polyimide coating 27 about 0.001 inch (0.025 mm) thick, which is jacketed on the distal taper section with a fluoropolymer coating 28, such as THV, of about 0.004 inch (0.102 mm) to about 0.005 inch (0.127 mm) thick. In the embodiment illustrated in FIG. 2, coating 27 extends distally to a point distal to the shaft 11 distal end and proximal to the distal end of core member 20.

Figure 5:
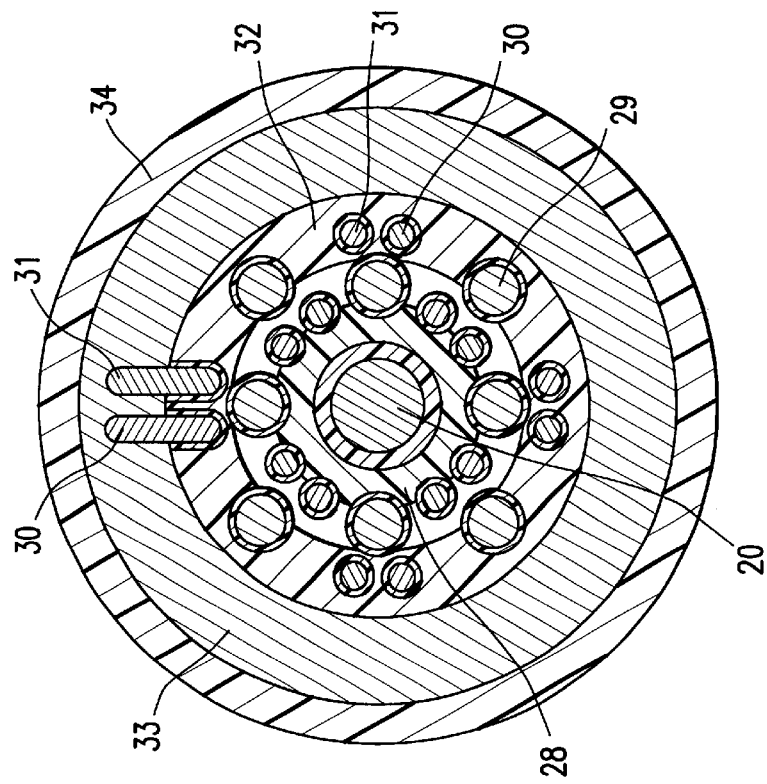
FIG. 5 is a transverse cross-sectional view of the EP device shown in FIG. 3 taken along the lines 5—5.
Figure 4:
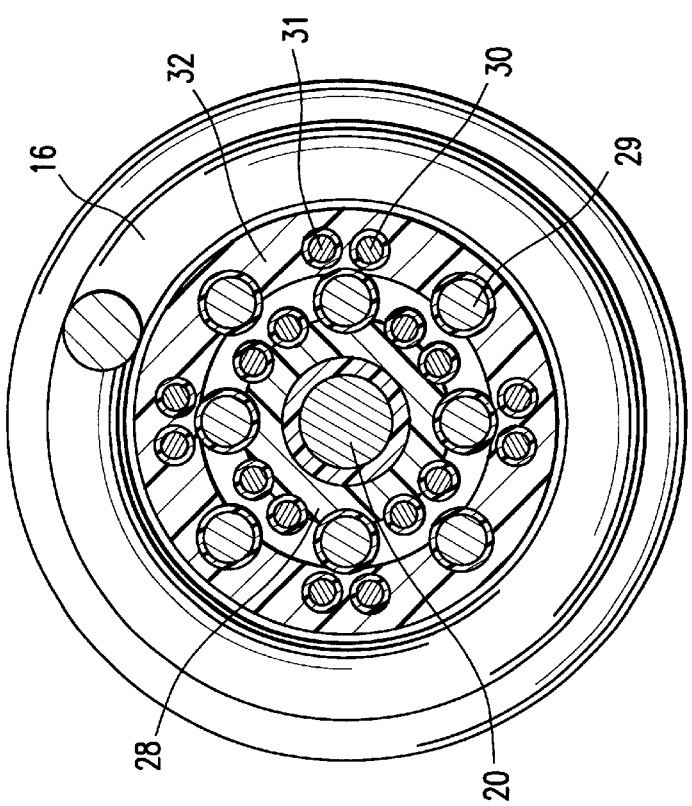
FIG. 4 is a transverse cross-sectional view. of the EP device shown in FIG. 3 taken along the lines 4—4.

In the embodiment illustrated in FIGS. 1–5, the electrodes 16 are helical coils which are electrically connected to insulated electrical conductors 29. The temperature sensors 17 are thermocouples formed by thermocouple wires 30 and 31. As best illustrated in FIGS. 4 and 5, showing transverse cross sections of the device shown in FIG. 3 taken along lines 4—4 and 5—5, the braided electrical conductors 29 are formed of 36 AWG copper wire with each conductor having a polyimide insulating coating of about 0.0005 inch thick (0.013 mm). The thermocouple wires are formed of 41 AWG copper and constantan with each wire having a polyimide insulating coating of about 0.00025 inch (0.007 mm) to about 0.0005 inch (0.013 mm) thick.

The shaft 11 comprises a braided structure formed by the electrical conductors 29 and the thermocouple wires, at least partially coated with a jacket 32. In a presently preferred embodiment, the jacket 32 is a fluoropolymer such as THV. In the presently preferred embodiment illustrated in FIG. 1, braided electrical conductors 29 and the thermocouple wires 30, 31 are also at least partially within the coating 28 around the core member 20.

A conducting member 33 covers the outer surface of the temperature sensors 17. The conducting member 33 is preferably a gold band, of about 0.001 inch (0.025 mm) to about 0.005 inch (0.13 mm) thick, and preferably about 0.002 inch (0.05 mm) thick, disposed about the shaft 11, and is connected to the temperature sensors 17 by suitable material such as gold-tin solder. In the presently preferred embodiment illustrated in FIG. 1, a fluoropolymer jacket 34, preferably formed from THV, covers the conducting member 33 and insulates the temperature sensor 17 from noise (e.g. RF noise) present as a result of the energy sent to the electrodes. The jacket 34 may cover at least part of the electrodes 16, as for example, the edges of the individual electrodes to prevent exposure of a sharp metallic edge of the electrode. In an alternative embodiment (not shown), the jacket 34 may be omitted as, for example, where filtering capability is provided which filters out the signal noise. More direct contact with the lesion site results from the omission of the jacket 34, so that faster and more accurate temperature measurements are provided. Similarly, the thermocouple may be attached directly to the electrode coil for a faster and more accurate response, where the noise from the electrode energy is otherwise filtered.

In the presently preferred embodiment illustrated in FIG. 1, the distal ends of the thermocouple wires are joined together so that the thermocouple formed therefrom measures the temperature at the interface of the two wires. Alternatively, the distal ends of the thermocouple wires may be individually secured to the conducting member 33 in a spaced apart configuration so that the thermocouple measures the temperature along the length of the conducting member 33 between the distal ends of the thermocouple wires.

The maximum outer dimensions of the electrodes are generally about 1.0 mm (3 Fr) to about 1.3 mm (4 Fr), and preferably about 1.22 mm (3.7 Fr). The electrode length is about 2 mm to about 8 mm, and preferably about 6 mm. The interelectrode spacing must be large enough to accommodate a temperature sensor, and is generally about 1 mm to about 3 mm, and preferably about 2 mm. In a presently preferred embodiment, about 4 to about 12 individual electrodes are provided on the shaft distal section, however, the device may have larger number of electrodes if the diameter of the distal section is increased to greater than 5 Fr.

The EP device 10 has a total length, including the connector 14, of about 100 cm to about 200 cm, and preferably about 165 cm. The length of the distal shaft section 13 having electrodes 16 is about 2 cm to about 15 cm, and preferably about 6 cm.

The EP device 10 may be introduced into the patient's vascular system, e.g. the femoral vein, percutaneously or by way of a cut-down, within a guiding member. Typically, the device is used to make a linear ablation within the patients atrium, although it may also be used to create lesions within a ventricle. The device is typically advanced through the inferior vena cava until the distal section 13 is disposed within the right atrium. The device may alternatively be advanced into the left atrium through a transseptal venous sheath, or retrogradely through the aorta and left ventricle via a femoral artery access site. Torquing the proximal section 12 of the device 10, which extends out of the patient during the procedure, will cause the distal section 13 thereof to be rotatably displaced within the atrial chamber and allow the EP device 10 to be properly positioned so electrical activity can be detected and heart tissue can be ablated at a number of locations within the chamber. When sensing electrical activity essentially all of the electrodes 16 can be simultaneously employed, but, when performing an ablation, the typical procedure is to direct the RF current to one or two electrodes at the most distal end of the EP device to perform the first ablation and then continue proximally one or two electrodes at a time until an ablation of desired length is obtained in the atrial chamber. This reduces the overall power requirements for the assembly. The temperature sensors detect the temperature of the heart wall between the adjacent electrodes, so that the electrical power delivered to each electrode can be controlled by a suitable device (not shown) to control the temperature in a desired manner, and to gauge when a continuous lesion has been formed and, therefore, when to move proximally to the next electrodes. However, simultaneous delivery of RF energy to a select number or all electrodes is possible with the use of a multiple channel temperature sensing device, and a sufficient power source.

Feedback of the temperature data can be used to modulate the power and prevent thrombus in the preferred use. Cooling fluid could alternatively be used as described in copending application, Ser. No. 08/629,057.

After the ablation, the electrodes 16 can be employed to detect electrical activity to ensure that the ablation has been effective in terminating the fibrillation or flutter. Typically, the elongated lesion formed with the device of the present invention is about 3 to about 12 mm, usually about 5 to about 10 mm, in width.

The electrical connector 14 on the proximal end of the device may be a commercially available electrical connector such as Part No. PAB-M08-GLA39J or PAB-M08-TLA39J for an eight pin connector or Part No. PAB-M08-GLA39A for a connector with a greater number of pins, e.g. 9–16. The above connectors are available from Lemo USA, Inc. in Santa Rosa, Calif. Suitable connectors for accessory cables connectable to the above connectors include PRB-M08-GLL65J for eight pin connectors and PRB-M08-GII65A for connectors with more than eight pins. The latter connectors are also available from the same source.

While the invention has been described herein in terms of certain preferred embodiments directed to the detection and treatment of atrial fibrillation and flutter, those skilled in the art will recognize that the invention may be employed in a wide variety of procedures where an elongated lesion is to be formed. Moreover, although individual features of embodiments of the invention may be shown in some of the drawings and not in others, those skilled in the art will recognize that individual features of one embodiment of the invention can be combined with any or all the features of another embodiment. A variety of modifications and improvements may be made to the present invention without departing from the scope thereof.

What is claimed is:

1. An electrophysiology device, comprising:
   a) an elongated shaft having a proximal end, a distal end, and a distal shaft section;
   b) a plurality of tubular coil electrodes on an exterior portion of the distal shaft section, having an interelectrode spacing of about 1 mm to not greater than 3 mm;
   c) at least one temperature sensor on an exterior portion of the distal shaft section, being positioned so that the temperature sensor is disposed between two adjacent electrodes;
   d) a metal band adjacent to and radially disposed about an outer surface of the temperature sensor and shaft; and
   e) one or more electrical conductors electrically connected to the at least one temperature sensor, at least partially embedded and hectically disposed within a wall of the elongated shaft.

2. The device of claim 1 further including a plurality of electrode electrical conductors which are each electrically connected to an individual electrode at a distal end of the electrode electrical conductor and having a proximal end configured to connect to an electrical source.

3. The device of claim 2 wherein the shaft has an elongated core member disposed therein.

4. The device of claim 3 further including a jacket disposed about the core member.

5. The device of claim 4 having the electrode electrical conductors at least in part helically braided into the core member jacket.

6. The device of claim 5 having the electrode electrical conductors at least in part helically braided into the shaft.

7. The device of claim 3 further including a distal tip member secured to the distal end of the shaft.

8. The device of claim 7 wherein the distal tip member includes a coil member disposed about a distal extremity of the core member distal to the shaft.

9. The device of claim 2 wherein the shaft has a lumen extending therein configured to slidably receive a guidewire therein.

10. The device of claim 2 wherein the electrode electrical conductors are helically braided into the shaft.

11. The device of claim 1 further including a jacket disposed on and about the metal band.

12. The device of claim 11 wherein the jacket is in part disposed about a periphery of the two electrodes adjacent to the temperature sensor.

13. The device of claim 4 wherein the jacket is disposed about and in contact with the metal band, and defines an outer surface of the electrophysiology device.

14. The device of claim 11 wherein the jacket is in part disposed about a periphery of at least one of the two electrodes adjacent to the temperature sensor.

15. The device of claim 1 wherein the electrodes are sensing and ablation electrodes.

16. The device of claim 1 wherein the distal shaft section has a maximum outer dimension less than 1.65 mm.

17. The device of claim 1 wherein the metal band is soldered to the temperature sensor.

18. An electrophysiology device assembly, comprising:
    a) a guiding member having an elongated shaft having a proximal end, a distal end, a port in the proximal end, a port in a distal shaft section, and a lumen extending therein; and
    b) an electrophysiology device slidably disposed in the lumen of the guiding member, comprising:
       an elongated shaft having a proximal end, a distal end, and a distal shaft section, and a plurality of electrical conductors helically braided into the shaft;
       a plurality of tubular coil electrodes on an exterior portion of the distal shaft section electrically connected to the electrical conductors, having an interelectrode spacing of about 1 mm to not greater than 3 mm;
       a plurality of temperature sensors on an exterior portion of the distal shaft section, being positioned so that at least one temperature sensor is disposed between two adjacent electrodes, each temperature sensor being electrically connected to at least one of the electrical conductors helically braided into the shaft; and
       a plurality of metal bands on the shaft, so that a metal band is adjacent to and radially disposed about an outer surface of each temperature sensor and the shaft.

19. The assembly of claim 18 wherein the guiding member distal shaft section is shapeable.

20. A method for treating a patient, comprising:
    a) providing an electrophysiology device, comprising:
       an elongated shaft having a proximal end, a distal end, and a distal shaft section, and a plurality of electrical conductors helically braided into the shaft;
       a plurality of tubular coil electrodes on an exterior portion of the distal shaft section electrically connected to the electrical conductors, having an interelectrode spacing of about 1 mm to not greater than 3 mm; and
       a plurality of temperature sensors on an exterior portion of the distal shaft section, being positioned so that at least one temperature sensor is disposed between two adjacent electrodes, each temperature sensor being electrically connected to at least one of the electrical conductors helically braided into the shaft; and
       a plurality of metal bands on the shaft, so that a metal band is adjacent to and radially disposed about an outer surface of each temperature sensor and the shaft;
    b) introducing the device into the patient's vasculature and advancing the device until the distal section of the device is disposed within a chamber of the patient's heart;
    c) placing at least one electrode on the device distal shaft section in contact with a desired surface of the heart chamber; and
    d) delivering high frequency electrical energy to the at least one electrode on the device and measuring the temperature at a temperature sensor adjacent the electrode.

21. The method of claim 20 further including before step (a), providing an elongated guiding member having proximal and distal ends, an inner lumen extending therein to the distal end configured to slidably receive the electrophysiology device, and a port on a distal section in communication with the inner lumen, and introducing the guiding member into the patient's vasculature and advancing the distal end of the guiding member to a chamber of the patient's heart.

22. The method of claim 20 wherein the patient is treated for heart fibrillation or flutter.

23. The method of claim 20 including placing at least two adjacent electrodes on the device distal shaft section in contact with a desired surface of the heart chamber, and delivering high frequency electrical energy to the two adjacent electrodes on the device, and measuring the temperature at a temperature sensor between the two electrodes, to form a first lesion and a second lesion continuous with the first lesion on the surface of the heart chamber.

24. An electrophysiology device for use within a patient's heart, comprising:
   a) an elongated shaft having proximal and distal ends; and
   b) a distal shaft section including a plurality of longitudinally disposed tubular coil electrodes on an exterior portion thereof, the electrodes having a maximum outer diameter of about 1 mm to about 1.22 mm and a length of about 2 mm to about 8 mm and an interelectrode spacing of about 1 mm to not greater than 3 mm, at least one temperature sensor disposed on an exterior portion of the distal shaft section between two adjacent electrodes, and a plurality of individually insulated electrical conductors at least partially embedded and helically disposed within a wall of the elongated shaft each electrode and the at least one temperature sensor being electrically connected to at least one electrical conductor.

25. The electrophysiology device of claim 24 including an inner lumen extending within the elongated shaft, configured to slidably receive a device therein.

26. The electrophysiology device of claim 24 including a core member extending within the elongated shaft.

27. The electrophysiology device of claim 26 wherein the electrical conductors are disposed about the core member.

28. The electrophysiology device of claim 24 wherein the electrical conductors form at least part of a wall of the distal shaft section.

29. The electrophysiology device of claim 24 including a source of high frequency electrical energy electrically connected to the electrical conductors.

30. An electrophysiology device, comprising:
   a) an elongated shaft having a proximal end, a distal end, and a distal shaft section;
   b) a plurality of electrodes on an exterior portion of the distal shaft section; and
   c) a plurality of temperature sensors on an exterior portion of the distal shaft section, being positioned so that at least one temperature sensor is disposed between two adjacent electrodes, and each temperature sensor having a conducting member comprising an annular metal band radially disposed about and adjacent to the shaft and the temperature sensor thereon, which transmits heat to the temperature sensor, and a jacket radially disposed on and about an outer surface of the metal band.

31. An electrophysiology device, comprising:
   a) an elongated shaft having a proximal end, a distal end, and a distal shaft section;
   b) a plurality of electrodes on an exterior portion of the distal shaft section;
   c) at least one temperature sensor on an exterior portion of the distal shaft section, being positioned so that the temperature sensor is disposed between two adjacent electrodes;
   d) a conducting member connected to the temperature sensor; and
   e) a jacket disposed about the conducting member and a periphery of at least one of the two electrodes adjacent to the temperature sensor.

32. An electrophysiology device, comprising:
   a) an elongated shaft having a proximal end, a distal end, and a distal shaft section;
   b) a plurality of electrodes on an exterior portion of the distal shaft section;
   c) at least one temperature sensor on an exterior portion of the distal shaft section, being positioned so that the temperature sensor is disposed between two adjacent electrodes; and
   d) a jacket disposed about the at least one temperature sensor and in part disposed about a periphery of the two electrodes adjacent to the at least one temperature sensor.

33. The device of claim 32 wherein the jacket is an electrically insulating material.

34. An electrophysiology device, comprising:
   a) an elongated shaft having a proximal end, a distal end, and a distal shaft section;
   b) a plurality of tubular coil electrodes on an exterior portion of the distal shaft section having an interelectrode spacing of about 1 mm to not greater than 3 mm;
   c) at least one temperature sensor on an exterior portion of the distal shaft section, being positioned so that the temperature sensor is disposed between two adjacent electrodes;
   d) one or more electrical conductors electrically connected to the at least one temperature sensor, at least partially embedded and helically disposed within a wall of the elongated shaft.

35. An electrophysiology device, comprising:
   a) an elongated shaft having a proximal end, a distal end, and a distal shaft section;
   b) a plurality of tubular coil electrodes on an exterior portion of the distal shaft section, having an interelectrode spacing of about 1 mm to not greater than 3 mm;
   c) at least one temperature sensor on an exterior portion of the distal shaft section, being positioned so that the temperature sensor is disposed between two adjacent electrodes;
   d) a conducting member disposed about an outer surface of the temperature sensor; and
   e) one or more electrical conductors electrically connected to the at least one temperature sensor, at least partially embedded and helically disposed within a wall of the elongated shaft.

* * * * *

UNITED STATES PATENT AND TRADEMARK OFFICE
CERTIFICATE OF CORRECTION

PATENT NO.    : 6,251,107 B1
DATED         : June 26, 2001
INVENTOR(S)   : Alan K. Schaer It is certified that error appears in the above-identified patent and that said Letters Patent is hereby corrected as shown below:

<u>Column 7,</u>
Line 31, change "hectically" to -- helically --.

Signed and Sealed this

Twenty-third Day of April, 2002

Attest:

Attesting Officer

JAMES E. ROGAN
*Director of the United States Patent and Trademark Office*